United States Patent [19]

Phelps et al.

[11] Patent Number: 5,256,651
[45] Date of Patent: Oct. 26, 1993

[54] HYDROPHILIC-HYDROPHOBIC DERIVATIVES OF POLYGALACTOMANNANS CONTAINING TERTIARY AMINE FUNCTIONALITY

[75] Inventors: Martha A. Phelps; Michael E. Morgan, both of Louisville, Ky.

[73] Assignee: Rhone-Poulenc, Inc., Cranbury, N.J.

[21] Appl. No.: 890,293

[22] Filed: May 27, 1992

Related U.S. Application Data

[63] Continuation of Ser. No. 643,343, Jan. 22, 1991, abandoned.

[51] Int. Cl.⁵ .................... A61K 31/715; C08B 37/00; C07H 15/04
[52] U.S. Cl. ........................... 514/53; 514/54; 536/114; 536/120; 536/123; 536/123.1; 252/8.551; 507/115; 8/929
[58] Field of Search ............ 536/114, 120, 123, 123.1; 514/53, 54

[56] References Cited

U.S. PATENT DOCUMENTS

| | | | |
|---|---|---|---|
| 4,870,167 | 9/1989 | Zody et al. | 536/114 |
| 4,918,181 | 4/1990 | Karcher et al. | 536/114 |
| 4,933,284 | 6/1990 | Lapins et al. | 536/63 |

Primary Examiner—Johnnie R. Brown
Assistant Examiner—Everett White
Attorney, Agent, or Firm—Herbert P. Price

[57] ABSTRACT

Triple derivatives of polygalactomannan i.e., dialkylaminoalkyl ether-hydroxyalkyl ether - long aliphatic chain ether of polygalactomannan, are useful as thickening agents for aqueous fluids.

24 Claims, No Drawings

HYDROPHILIC-HYDROPHOBIC DERIVATIVES OF POLYGALACTOMANNANS CONTAINING TERTIARY AMINE FUNCTIONALITY

This is a continuation of Ser. No. 643,348 filed Jan. 22, 1991, abandoned.

BACKGROUND OF THE INVENTION

The field of art to which this invention is directed is polysaccharide derivatives.

Polygalactomannans, particularly the naturally occurring guar gum and locust bean gum, have been known for some time and have found many industrial uses. To improve the performance of these gums and to widen their fields of use, polygalactomannans have been modified by reaction with various reagents to form derivatives of the gums. Examples of such derivatives are hydroxyalkyl ethers of polygalactomannans, aminoalkyl ethers of polygalactomannans, long chain alkyl ethers-hydroxyalkyl ethers of polygalactomannans, and aminoalkylether-hydroxyalkyl ethers of polygalactomannans.

Hydroxyalkyl ethers of polygalactomannans are described in U.S. Pat. No. 3,326,890. Aminoalkyl ethers of the gums are disclosed in U.S. Pat. No. 3,498,412. Mixed derivatives containing long chain alkyl ether groups and hydroxyalkyl ether groups are described in U.S. Pat. No. 4,870,167. Mixed derivatives containing tertiary aminoalkyl ether groups and hydroxyalkyl ether groups are disclosed in U.S. Pat. No. 4,918,181.

Hydrophobically-hydrophilically modified polygalactomannans are disclosed in U.S. Pat. No. 4,960,876.

Hydrophobe substituted water-soluble polysaccharides which contain quaternary ammonium substituents are described in U.S. Pat. No. 4,663,159.

Polygalactomannans and their derivatives find extensive use as thickeners for aqueous systems in many industrial applications. As disclosed in U.S. Pat. No. 4,870,167, hydrophobically modified non-ionic polygalactomannans are efficient thickeners for aqueous fluids, either alone or combined with surfactants.

After the purpose for using the thickened aqueous fluid has been served, it is often desirable to lower the viscosity of the fluid. This lowering of viscosity is accomplished by using a "breaker" which acts on the water-soluble polymer to reduce its molecular weigh and to thin the fluid in which it is dissolved.

In commonly assigned U.S. Pat. No. 4,647,385, the viscosity of aqueous solutions of water-soluble polymers is reduced by the addition of alkali metal or alkaline earth metal salts of hypochlorous acid plus tertiary amines.

When tertiary amino polygalactomannans or the double derivative, i.e., dialkylaminoalkyl-hydroxyalkyl ethers of polygalactomannans, are used, as thickeners for aqueous fluids, the viscosity of the fluids can be reduced by the addition of an alkali metal or alkaline earth metal salt of hypochlorous acid, or a chlorinated isocyanurate. These reactions are disclosed in commonly assigned U.S. Pat. No. 4,941,537 and U.S. Pat. No. 4,918,181.

SUMMARY OF THE INVENTION

This invention is directed to derivatives of polygalactomannans. In one aspect, this invention pertains to a triple derivative of a polygalactomannan. In another aspect, this invention relates to thickened aqueous fluids made from the triple derivative. In still another aspect, this invention pertains to a process for reducing the viscosity of thickened aqueous fluids.

The composition of this invention is a dialkylaminoalkyl ether-hydroxyalkyl ether-long aliphatic chain ether of a polygalactomannan. Each of the alkyl groups in the dialkyl aminoalkyl ether contain 1 to 6 carbon atoms wherein the total number of carbon atoms does not exceed 12. The alkyl group of the hydroxyalkyl ether contains 2 to 4 carbon atoms. The long aliphatic chain ether group contains 8 to 28 carbon atoms.

The degree of substitution of the dialkylaminoalkyl ether group is about 0.001 to about 0.2. The molecular substitution of the hydroxyalkyl ether group is about 0.2 to about 2. The molecular substitution of the long aliphatic chain ether group is about 0.001 to about 0.2

The composition of this invention can be used to thicken and gel aqueous fluids for various applications. Such applications include the fracturing of subterranean formations penetrated by a borehole, for use in oil and gas well drilling, completion and work over fluids, and in personal care, carpet dying and waste treatment processes. When desired, the viscosity of the thickened or gelled fluids is reduced by the addition of alkali metal or alkaline earth metal salts of hypochlorous acid or a chlorinated isocyanurate.

DESCRIPTION OF THE INVENTION

The water soluble polymers of this invention are triple derivatives of polygalactomannans, i.e., dialkylaminoalkyl ether, hydroxyalkyl ether, long aliphatic chain ether derivatives.

The polygalactomannans from which the triple derivatives are made are hydrocolloid polysaccharides composed principally of galactose and mannose units and are usually found in the endosperm of leguminous seeds, such as guar, locust bean, honey locust, flame tree, and the like. Guar, for example, is composed mostly of a galactomannan which is essentially a straight chain mannan with single-membered galactose branches. The mannose units are linked in a 1,4-B-glycosidic linkage and the galactose branching takes place by means of a 1-6 linkage on alternate mannose units. The ratio of galactose to mannose units in the guar polymer is one to two.

Locust bean gum is also a polygalactomannan of similar molecular structure in which the ratio of galactose to mannose is one to four. Guar and locust bean gum are the preferred sources of the polygalactomannans, principally because of their commercial availability.

The dialkyl amino alkyl derivatizing agents useful in this invention are dialkylaminoalkyl halides or epoxides wherein each alkyl group contains from 1 to 6 carbon atoms and wherein the total number of carbon atoms does not exceed 12. The halides being chloride, bromide, and iodide with the chloride being preferred.

Examples of useful dialkylamino alkyl derivatizing agents are dimethylaminomethyl chloride, dimethylaminoethyl chloride, dimethylaminopropyl chloride, methylethylaminopropyl bromide, dimethylaminoisopropyl chloride, methylethylaminoisopropyl chloride, dimethylaminobutyl iodide, 3-dimethylamino-1,2-epoxypropane, 3-diethylamino-1,2-epoxypropane, and other isom The hydroxyalkyl derivatizing agents useful in this invention are alkylene oxides, wherein the alkylene group contains from two to four carbon atoms and the epoxide group is on adjacent carbon atoms. Examples of alkylene oxides are ethylene oxide, propylene oxide-1,2,butylene oxide 1,2, and butylene oxide-2,3. The preferred alkylene oxide is propylene oxide-1,2.

The other derivatizing agent used in this invention is a long aliphatic chain epoxy compound which contains from about 8 to about 28 carbon atoms or an alkyl halide having about 8 to about 28 carbon atoms in the alkyl group. Examples of such epoxy compounds are 1,2-epoxyoctane, 1,2-epoxydodecane, 1,2-epoxyhexadecane, 1,2-epoxytetracosane, and the like. Other long chain epoxy compounds are glycidyl ethers of aliphatic alcohols wherein the aliphatic alcohols contain about 5 to about 25 carbon atoms. Examples of such glycidyl ethers are the glycidyl ethers of amyl alcohol, hexanol, octanol, lauryl alcohol, stearyl alcohol, lignoceryl alcohol and the like. Exmaples of useful alkyl halides are octyl chloride, decyl bromide, dodecyl iodine, hexadecyl bromide and the like.

In preparing the compositions of this invention, the hydrophilic group reagent, i.e., the 2 to 4 carbon alkylene oxide, is reacted first, followed by reaction with the hydrophobic group reagent, i.e., the long aliphatic chain epoxide or halide, and then the dialkylamino alkyl ether reagent.

The reaction of short chain alkylene oxides with polygalactomannans is described in detail in U.S. Pat. Nos. 3,326,890 and 3,723,409, which are hereby incorporated by reference. The reaction of hydroxyalkyl ethers of polygalactomannans with long aliphatic chain reagents is described in detail in U.S. Pat. No. 4,870,167, which is hereby incorporated by reference. The reaction of polygalactomannans with dialkylaminoalkyl halides or epoxides is described in U.S. Pat. No. 3,498,912, which also is incorporated by reference.

The polygalactomannan can be reacted with the hydrophilic derivatizing agents in powder or granular form, or in the form of splits. The reactions can be conducted in aqueous, non-aqueous, or mixed systems using alkali as the condensing or catalytic agent. When using powder or granular polygalactomannans, preferred reaction media are lower alcohol-water mixtures, e.g., methanol or isopropanol, and water. The preferred medium for reacting splits is water.

It is necessary in order for the second reaction to take place that the hydrophobic reagent be compatible with the hydrophilic derivatized polygalactomannan. To obtain the required compatibility, a solvent which is miscible with the hydrophobic reagent and which swells the hydrophobically substituted polygalactomannan without dissolving it is needed. The solvent is miscible with water in the amount of at least 10 weight percent water-in-solvent or solvent-in-water, and which has a solubility parameter greater than 4.5 $(J/m^3)^{\frac{1}{2}} \times 10^{-3}$. Solubility parameter is described in detail in Kirk-Othmer, "Encyclopedia of Chemical Technology," 3rd Edition, Volume 21 (1983) beginning at page 377, which is hereby incorporated by reference. Examples of suitable solvents are 1-propanol, 2-propanol, t-butanol, propylene oxide, tetrahydrofuran, dimethyl sulfoxide, N,N-dimethyl formamide, methanol, ethanol, ethylene glycol, ethylene glycol monomethyl ether, ethylene glycol monobutyl ether, propylene glycol, propylene glycol monoethyl ether, methyl ethyl ketone, and acetone. Preferred solvents are the solvents which contain an aliphatic hydroxyl group, with the more preferred being secondary or tertiary hydroxyl groups. The most preferred solvent is 2-propanol. The amount of solvent used is at least equal to the weight of the hydrophobic derivatizing agent, up to about 10 times its weight, preferably about 2 to about 5 times its weight.

When the hydrophobic derivatization reaction is complete, the reaction with the tertiary amine derivatizing agent is conducted.

The catalysts used in these derivatizing reactions are alkaline catalysts, e.g., sodium or potassium hydroxide. The amount of catalyst will vary from about 0.1 to about 5 weight percent based on the weight of the polygalactomannan. When the derivatizing agent is a halide, then the amount of alkali used is at least equivalent to the halide in the derivatizing agent, and preferably, in excess of the halide.

Molecular substitution (MS) of the hydrophilic hydroxyalkyl group is about 0.2 to about 2 and, preferably, about 0.5 to about 1.5. The molecular substitution of the long aliphatic chain group is about 0.001 to about 0.2 and, preferably, about 0.005 to about 0.1. The degree of substitution of the dialkylaminoalkyl group is about 0.001 to about 0.2 and, preferably, about 0.004 to about 0.1

The viscosity of aqueous solutions of the compositions of this invention is enhanced by the addition of surfactants. The viscosity is increased by the addition of very small amounts of surfactant, i.e., 1 drop of surfactant in 400 mls of a 0.5 weight percent aqueous solution of the gum. Generally about 10 ppm of surfactant up to about 1 weight percent of surfactant is used based on the weight of the aqueous solution. Preferably, about 0.01 to about 0.2 weight percent is used.

Any water soluble surfactant can be used in this invention. The preferred surfactants have an HLB of at least 7 and, more preferably, at least 10.

Examples of suitable anionic surfactants are alkali metal, ammonium and amine soaps, such as sodium and potassium myrisate, laurate, palmitate, oleate, stearate, resinate and hydroabietate, the alkali metal alkyl or alkylene sulfates, such as sodium lauryl sulfate, potassium stearyl-sulfate, the alkali metal alkyl or alkylene sulfonates, such as sodium lauryl sulfonate, potassium stearyl sulfonate, and sodium cetyl sulfonate, sulfonated mineral oil, as well as the ammonium salts thereof.

Other examples of suitable anionic surfactants are alkali metal salts of alkyl-aryl sulfonic acids, sodium dialkyl sulfosuccinate, sulfated or sulfonated oils, sulfonated tallow and alkali salts of short chain petroleum sulfonic acids.

Examples of nonionic surfactants are condensation products of higher fatty alcohols with ethylene oxide, such as the reaction of oleyl alcohol with 10 ethylene oxide units, condensation products of alkyl phenols with ethylene oxide, such as the reaction product of isooctylphenol with 12 ethylene oxide units; condensation products of higher fatty acid amides with 5 or more ethylene oxide units; polyethylene glycol ethers of long chain fatty acids, such as teraethylene glycol monopalmitate, ethylene oxide condensation products of polyhydric alcohol partial higher fatty esters, and their inner anhydrides (mannitol-anhydride, called Mannitan and sobitol-anhydride called Sorbitan), and glycerol monopalmitate reacted with 10 molecules of ethylene oxide; long chain polyglycols in which one hydroxyl groups is esterified with a higher fatty acid and the other hydroxyl group is etherified with a low molecular weight alcohol, such as methoxypolyethylene glycol 550 monostearate (550 being the average molecular weight of the polyglycol ether). A combination of two or more of these surfactants can be used.

The compositions of this invention in aqueous solutions can be crosslinked using any of the known crosslinkers for polygalactomannans. Examples of such crosslinkers are boron compounds, e.g., borax, transition metal chelates and salts, e.g., titanium, zirconium and antimony compounds.

The compounds of this invention are particularly useful in the process of fracturing subterranean formations penetrated by a borehole. In this process, a water based fluid is injected into the borehole and into contact with the formation at a rate and pressure sufficient to fracture the formation. The water based fluid is made from (a) an aqueous liquid, (b) as a thickening agent to increase the viscosity of the aqueous liquid, a viscosity increasing amount of the composition of this invention, and (c) as a breaker to reduce the viscosity of the fluid after the fluid has contacted the formation and after its intended purpose as a viscous fluid has been served, an effective amount of a reducing agent.

In the fracturing process, about 10 to about 80 pounds of derivatized polygalactomannan are used per 1000 gallons of aqueous fluid, and preferably, about 20 to about 60 pounds.

After its intended purpose has been served, e.g., when the fracturing process has been completed, the viscosity of the aqueous fluids is reduced by adding to the solutions alkali metal and alkaline earth metal salts of hypochlorous acid, or chlorinated isocyanurate. The hypochlorite salts include magnesium hypochlorite, calcium hypochlorite, and lithium hypochlorite. The preferred salts are sodium and calcium hypochlorite.

The chlorinated isocyanurate useful in this invention include trichloro-s-triazine trione, sodium dichloro-s-triazine trione, potassium dichloro-s-triazine trione, sodium dichloro-s-triazine trione dihydrate, and mixtures thereof.

The reduction in viscosity of aqueous fluids made according to this invention, is conducted on aqueous fluids which are thickened with about 10 to about 80 pounds polygalactomannan per 1000 gallons of aqueous fluid. Preferably, the amount of triple derivative polygalactomannan will be about 20 to about 60 pounds per 1000 gallons.

The amount of metal hypochlorite or chlorinated isocyanurate used to reduce the viscosity of the thickened aqueous fluid will vary from about 0.1 to about 5 pounds per 1000 gallons of aqueous fluid and, preferably, about 0.5 to about 2 pounds per gallons.

The thickened aqueous fluid prior to the addition of the hypochlorite salt has a pH of about 6 to about 11 and, preferably, about 7 to about 10. The temperature of the system will vary from about 50° F. to about 300° F. The breaker systems of this invention are particularly useful at temperatures of about 70° to about 250° F.

The following examples describe the invention in more detail. Parts and percentages are by weight unless otherwise designated.

Example 1

To a suitable reactor were added 450 parts of hydroxypropyl guar having an MS of 1.2, 1000 parts of isopropanol and 90 parts of 1,2-epoxy hexadecane. The temperature was raised to 60° C. An additional 150 parts of isopropanol were added. The temperature was held at 60oC for 10 minutes to allow the derivatized guar to swell. Potassium hydroxide, 10 parts, was added and the temperature was held at 60° C. for 1.5 hours. After cooling to room temperature, the liquid was decanted from the derivatized guar. The derivatized guar was then washed twice with 1000 parts of acetone, was filtered and was allowed to air dry.

To a suitable reactor were added 45 parts of derivatized guar prepared above, 250 parts of isopropanol, 5 parts of potassium hydroxide and 3.9 parts of dimethylamino-propyl chloride hydrochloride. Heat was applied raising the temperature to 70° C. and holding it at 70° C. for 2 hours. After cooling to room temperature, the liquid was decanted from the triple derivatized guar and the product was washed with acetone and air dried.

A half percent solution of the triple derivative was made in deionized water and the pH was adjusted to 6.5 with formic acid. After hydrating for 2 hours, the pH was adjusted to 8.0 with formic acid. The viscosity was 450 cps using a Brookfield viscometer at 20 RPM. To 400 parts by volume of the solution were added 0.3 part by volume of a 28 percent solution of ammonium lauryl sulfate (ALS) in water. The viscosity was measured using the Brookfield viscometer at 20 RPM. After the viscosity measurement, several additions of a 3 percent solution of calcium hypochlorite (CHC), 0.9 part by volume for each addition, as well as another addition of ammonium lauryl sulfate was made. The viscosities were determined after each addition. The viscosity measurements were as follows:

| | |
|---|---|
| 2 hour viscosity | 450 cps |
| +0.3 part ALS solution | 3750 cps |
| +0.9 part CHC solution | 3700 cps |
| +0.9 part CHC solution | 900 cps |
| +0.9 part CHC solution | 50 cps |
| +0.3 part ALS solution | 720 cps |

After standing for 1 hour at room temperature, the viscosity was found to be 60 cps and the pH was 7.1.

Example 2

Using the same procedure described in Example 1, 90 parts of 1.2 MS hydroxypropyl guar 250 parts of isopropanol guar, 250 parts of isopropanol, 20 parts of 1,2-epoxy-hexadecane and 2 parts of potassium hydroxide were reacted. The double derivative reaction product, 45 parts, was reacted in 250 parts of isopropanol with 4.3 parts of dimethylaminopropyl chloride hydrochloride, and 5.2 parts of potassium hydroxide using the procedure described in Example 1.

Solutions of the triple derivative were prepared at 40 pounds per 1000 gallons of solution. The pH was adjusted to 6.5 with formic acid. After hydrating for 2 hours, the pH was adjusted to 8.0 with formic acid and the viscosity was measured with a Brookfield viscometer at 20 RPM. A 3 percent aqueous calcium hypochlorite solution was added on the basis of 0.9 ml to 400 ml of the aqueous fluid. After measuring the viscosity, another portion of calcium hypochlorite solution in the same amount was added and the viscosity was measured The viscosity measurements were as follows:

| | |
|---|---|
| 2 hour viscosity | 1925 cps |
| +CHC solution | 40 cps |
| +CHC solution | <10 cps |

Example 3

Using the same procedure described in Example 1, the double derivative of Example 2, 45 parts, was reacted in 250 parts of isopropanol with 4.3 parts of dimethylaminopropyl hydrochloride and 5.2 parts of potassium hydroxide. The viscosity of 0.5 percent solutions made with pH adjustments as described in Example 1 was determined after 4 hours hydration time and after additions of 3 percent calcium hypochlorite solutions.

| 4 hour viscosity | 800 cps |
|---|---|
| +0.9 ml/400 ml CHC | 75 cps |
| +0.9 ml/400 ml CHC | >10 cps |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A polygalactomannan containing three different ether substituents wherein the polygalactomannan is a dialkylaminoalkyl etherhydroxyalkyl ether - long aliphatic chain ether of a polygalactomannan wherein each of the alkyl groups in the dialkylaminoalkyl ether substituent contains from 1 to 6 carbon atoms and wherein the total number of carbon atoms in the alkyl groups does not exceed 12, wherein the alkyl group of the hydroxyalkyl ether substituent contains 2 to 4 carbon atoms, and wherein the aliphatic chain in the long aliphatic chain ether substituent contains 8 to 28 carbon atoms with or without a hydroxy group substituent.

2. The polygalactomannan of claim 1 wherein the degree of substitution (DS) of the dialkylaminoalkyl ether substituent is about 0.001 to about 0.2, wherein the molecular substitution (MS) of the hydroxyalkyl ether substitutent is about 0.2 to about 2 and wherein the MS of the long aliphatic chain ether substituent is about 0.001 to about 0.2.

3. The polygalactanannan of claim 2 wherein the DS of the dialkylaminoalkyl ether substituent is about 0.004 to about 0.1, wherein the MS of the hydroxyalkyl ether substituent is about 0.5 to about 1.5, and wherein the MS of the long aliphatic chain ether substituent is about 0.005 to about 0.1.

4. The polygalactamannan of claim 1 wherein the polygalactomannan is guar gum.

5. The polygalactamannan of claim 1 wherein the dialkylaminoalkyl ether substitutent is dimethylaminopropyl ether, wherein the hydroxyalkyl ether substituent is hydroxypropyl ether and wherein the long aliphatic chain ether substituent is hydroxyhexadecyl ether.

6. An aqueous fluid comprising a polygalactomannan containing three different ether substituents wherein the polygalactomannan is a dialkylaminoalkyl ether - hydroxyalkyl ether - long aliphatic chain ether of a polygalactomannan wherein each of the alkyl groups in the dialkylaminoalkyl ether substituent contains from 1 to 6 carbon atoms and wherein the total number of carbon atoms in the alkyl groups does not exceed 12, wherein the alkyl group of the hydroxyalkyl ether substituent contains 2 to 4 carbon atoms, and wherein the aliphatic chain in the long aliphatic chain ether substituent contains 8 to 28 carbon atoms with or without a hydroxy group substituent.

7. The aqueous fluid of claim 6 wherein the degree of substitution (DS) of the dialkylaminoalkyl ether substituent is about 0.001 to about 0.2, wherein the molecular substitution (MS) of the hydroxyalkyl ether substituent is about 0.2 to about 2 and wherein the MS of the long aliphatic chain ether substituent is about 0.001 to about 0.2.

8. The aqueous fluid of claim 6 wherein the DS of the dialkylaminoalkyl ether substituent is about 0.004 to about 0.1, wherein the MS of the hydroxyalkyl ether substituent is about 0.5 to about 1.5, and wherein the MS of the long aliphatic chain ether substituent is about 0.005 to about 0.1.

9. The aqueous fluid of claim 6 wherein the polygalactomannan is guar gum.

10. The aqueous fluid of claim 6 wherein the dialkylaminoalkyl ether substituent is dimethylaminopropyl ether, wherein the hydroxyalkyl ether substituent is hydroxypropyl ether and wherein the long aliphatic chain ether substituent is hydroxyhexadecyl ether.

11. The aqueous fluid of claim 6 wherein the polygalactomannan is present in the amount of about 10 to about 80 pounds per 1000 gallon of aqueous fluid.

12. The aqueous fluid of claim 11 wherein the polygalactomannan is present in the amount of about 20 to about 60 pounds per 1000 gallons.

13. A process for reducing the viscosity of an aqueous fluid thickened with a polygalactomannan containing three different ether substituents wherein the polygalactomannan is a dialkylaminoalkyl ether - hydroxyalkyl ether - long aliphatic chain ether of a polygalactomannan wherein each of the alkyl groups in the dialkylaminoalkyl ether substituent contains from 1 to 6 carbon atoms and wherein the total number of carbon atoms in the alkyl groups does not exceed 12, wherein the alkyl group of the hydroxyalkyl ether substituent contains 2 to 4 carbon atoms, and wherein the aliphatic chain in the long aliphatic chain ether substituent contains 8 to 28 carbon atoms with or without a hydroxy group substituent which comprises adding to the aqueous fluid an alkali metal or an alkaline earth metal salt of hypochlorous acid or a chlorinated isocyanurate.

14. The process of claim 13 wherein the degree of substitution (DS) of the dialkylaminoalkyl ether substituent is about 0.001 to about 0.2, wherein the molecular substitution (MS) of the hydroxyalkyl ether substituent is about 0.2 to about 2 and wherein the MS of the long aliphatic chain ether substituent is about 0.001 to about 0.2.

15. The process of claim 14 wherein the DS of the dialkylaminoalkyl ether substituent is about 0.004 to about 0.1., wherein the MS of the hydroxyalkyl ether substituent is about 0.5 to about 1.5, and wherein the MS of the long aliphatic chain ether substituent is about 0.005 to about 0.1.

16. The process of claim 13 wherein the polygalactomannan is guar gum.

17. The process of claim 13 wherein the dialkylaminoalkyl ether substituent is dimethylaminopropyl ether, wherein the hydroxyalkyl ether substituent is hydroxypropyl ether and wherein the long aliphatic chain ether substituent is hydroxyhexyldecyl ether.

18. The process of claim 13 wherein the alkali metal is sodium.

19. The process of claim 13 wherein the alkaline earth metal is calcium.

20. The process of claim 13 wherein the chlorinated isocyanurate is sodium dichloro-S-triazine trione.

21. The process of claim 13 wherein the aqueous fluid contains about 10 to about 80 pounds of polygalactomannan per 1000 gallons of aqueous fluid.

22. The process of claim 21 wherein the aqueous fluid contains about 20 to about 60 pounds of polygalactomannan per 1000 gallons of aqueous fluid.

23. The process of claim 13 wherein the alkali metal or alkaline earth metal salt of hypochlorous acid, or the chlorinated isocyanurate is added in the amount of about 0.1 to about 5 pounds per 1000 gallons of aqueous fluid.

24. The process of claim 23 wherein the alkali metal or alkaline earth metal salt of hypochlorous acid, or the chlorinated isocyanurate is added in the amount of about 0.5 to about 2 pounds per 1000 gallons of aqueous fluid.

* * * * *